United States Patent
Doerr

(10) Patent No.: US 12,035,995 B2
(45) Date of Patent: Jul. 16, 2024

(54) SYSTEM FOR GENERATING AN ALERT FOR A SYSTEMIC INFECTION

(71) Applicant: BIOTRONIK SE & Co. KG, Berlin (DE)

(72) Inventor: Thomas Doerr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 17/924,008

(22) PCT Filed: May 17, 2021

(86) PCT No.: PCT/EP2021/062907
§ 371 (c)(1),
(2) Date: Nov. 8, 2022

(87) PCT Pub. No.: WO2021/239481
PCT Pub. Date: Dec. 2, 2021

(65) Prior Publication Data
US 2023/0190102 A1    Jun. 22, 2023

(30) Foreign Application Priority Data

May 26, 2020   (EP) .................................. 20176393
Sep. 15, 2020  (EP) .................................. 20196095

(51) Int. Cl.
*A61B 5/00*     (2006.01)
*G08C 17/02*    (2006.01)

(52) U.S. Cl.
CPC ............ *A61B 5/0031* (2013.01); *G08C 17/02* (2013.01)

(58) Field of Classification Search
CPC ... A61B 5/0031; A61B 5/0015; A61B 5/0002; A61B 5/686; A61B 2560/0209; A61N 1/37276; A61N 1/37282; A61N 1/37258; A61N 1/37252; A61N 1/37254; A61N 1/37211; H04Q 9/00; H04W 52/0229;
(Continued)

(56) References Cited

U.S. PATENT DOCUMENTS

| | | | |
|---|---|---|---|
| 6,292,698 B1 * | 9/2001 | Duffin | A61N 1/37282 607/32 |
| 10,182,336 B1 | 1/2019 | Stockton et al. | |

(Continued)

OTHER PUBLICATIONS

International Search Report (PCT/ISA/210) and Written Opinion (PCT/ISA/237) mailed on Aug. 18, 2021, by the European Patent Office as the International Searching Authority for International Application No. PCT/EP2021/062907.

*Primary Examiner* — Adnan Aziz
(74) *Attorney, Agent, or Firm* — Buchanan Ingersoll & Rooney PC

(57) ABSTRACT

An implantable medical device comprises a functional device for carrying out a therapeutic or diagnostic function, and a communication device for communicating with a remote monitoring system. The communication device, at a start of initial operation of the implantable medical device, is enabled to establish a communication with said remote monitoring system. In this way an implantable medical device is provided which allows for including the implantable medical device in a remote monitoring while reducing a risk for a patient involved with attending to the patient for activating a remote monitoring function within the implantable medical device.

12 Claims, 3 Drawing Sheets

(58) Field of Classification Search
CPC ......... H04W 52/0254; H04W 52/0258; H04W 52/028; G08C 17/02; Y02D 30/70
See application file for complete search history.

(56) References Cited

U.S. PATENT DOCUMENTS

| | | | | |
|---|---|---|---|---|
| 2006/0189854 | A1* | 8/2006 | Webb | G16H 40/63 600/300 |
| 2008/0064980 | A1* | 3/2008 | Lee | A61B 5/0816 607/59 |
| 2008/0183227 | A1* | 7/2008 | Sutton | A61N 1/37276 607/60 |
| 2009/0062887 | A1* | 3/2009 | Mass | G08B 21/02 340/539.11 |
| 2010/0114510 | A1* | 5/2010 | Vaingast | G01R 31/3648 702/62 |
| 2011/0152970 | A1* | 6/2011 | Jollota | H04L 67/12 342/357.55 |
| 2011/0201944 | A1 | 8/2011 | Higgins et al. | |
| 2012/0229299 | A1* | 9/2012 | Skoldengen | A61N 1/37276 340/870.02 |
| 2013/0154851 | A1* | 6/2013 | Gaskill | G16H 40/67 340/870.02 |
| 2015/0148868 | A1* | 5/2015 | Shahandeh | A61N 1/37217 607/60 |
| 2016/0321400 | A1* | 11/2016 | Durrant | A61N 1/3904 |
| 2017/0056677 | A1 | 3/2017 | Zhang et al. | |
| 2017/0100036 | A1 | 4/2017 | Cinbis et al. | |
| 2018/0152972 | A1* | 5/2018 | Wu | H04W 52/0216 |
| 2018/0243577 | A1* | 8/2018 | Kivi | A61N 1/36014 |
| 2018/0332653 | A1* | 11/2018 | Oza | A61N 1/37252 |

* cited by examiner

SYSTEM FOR GENERATING AN ALERT FOR A SYSTEMIC INFECTION

CROSS-REFERENCE TO RELATED APPLICATIONS

This application is the United States National Phase under 35 U.S.C. § 371 of PCT International Patent Application No. PCT/EP2021/062907, filed on May 17, 2021, which claims the benefit of European Patent Application No. 20196095.2, filed on Sep. 15, 2020, and European Patent Application No. 20176393.5, filed on May 26, 2020, the disclosures of which are hereby incorporated by reference herein in their entireties.

TECHNICAL FIELD

The present invention concerns an implantable medical device according to the preamble of claim 1, a system including an implantable medical device and a method for operating an implantable medical device.

BACKGROUND

An implantable medical device of this kind comprises a functional device for carrying out a therapeutic or diagnostic function, and a communication device for communicating with a remote monitoring system.

An implantable medical device of the type described herein may, for example, be a sensing system that can be implanted in a patient's vessel, for example, to measure a parameter such as the body temperature or the heart rate of the patient. The sensing system can be used to monitor a patient's condition, for example, for observing and diagnosing a course of disease, wherein the implantable medical device is designed to communicate with the remote monitoring system (located outside of the patient) to transmit measurement results to the remote monitoring system. Alternatively, the implantable medical device may be designed as an implantable stimulation device, for example, with a pacemaker, neuro-stimulation function or an implantable insulin pump, or a diagnostic device, such as a diagnostic patch.

Generally, the implantable medical device may be any active medical device which is to be implanted into a patient and, in an implanted state, performs a therapeutic function (for example, a pacing function) or a diagnostic function (for example, a recording or sensing function) within the patient, wherein the implantable medical device generally shall remain within the patient over a prolonged period of time, for example several months or even years. The implantable medical device generally comprises a functional device in the form of an electronics unit, which is formed, for example, by a processor and serves to perform a function in an active operational state of the medical device, for example, a measurement function to measure a physiological parameter of a patient, for example the heart rate. To operate the functional device, the implantable medical device generally comprises an energy storage element, particularly in the form of an electric battery, which feeds the functional device and supplies it with power in its operational state.

Implantable medical devices may be operated in cooperation with a remote monitoring system, comprising, for example, one or multiple monitoring devices (so-called patient relay devices) which may serve to monitor operation of the implantable medical device at the home of a patient and hence remotely from a healthcare environment such as a hospital. Such remote monitoring system generally is in communication with, e.g., an information system (also denoted as patient information system), such as a centralized service center, which may, for example, process data received from the implantable medical device via the remote monitoring system and may provide information derived from the data to healthcare personnel, such as a physician in a hospital or the like. The information system hence in cooperation with the remote monitoring system allows for a continuous monitoring of the state of the patient, for example, a cardiac function of the patient if the implantable medical device is a cardiac device, such as a cardiac pacemaker or a defibrillator.

Generally, a remote monitoring system serves to monitor the implantable medical device in an implanted state within a patient. Within the monitoring, data may be received at the remote monitoring system from the implantable medical device, the data relating to functions performed by the implantable medical device or to sensing data which are sensed and recorded by the implantable medical device and hence may relate to a state of the implantable medical device or, generally, the patient.

Nowadays, if an implantable medical device shall cooperate with a remote monitoring system, the implantable medical device needs to be specifically enabled to communicate with the remote monitoring system. Herein, for enabling the communication, a patient carrying an implanted medical device typically needs to visit a physician, such that the physician may access the implantable medical device using a suitable programming interface to activate a communication with the remote monitoring system.

Hence, if an implantable medical device shall be included in a remote monitoring, it needs to be specifically activated, which generally with common solutions requires the patient to visit a physician. Hence, if an implantable medical device shall be included in a home monitoring, this may represent logistical issues, and in addition may pose a risk to a patient, in particular in a situation of a general pandemic such as the COVID-19 pandemic. In particular in view of the fact that patients carrying implantable medical devices may be assumed to form a particular risk group, there is a general desire to alleviate any risks for such patients which are potentially linked to leaving a home environment.

The present disclosure is directed toward overcoming one or more of the above-mentioned problems, though not necessarily limited to embodiments that do.

SUMMARY

It is an object of the instant invention to provide an implantable medical device, a system and a method for operating an implantable medical device which allow for including an implantable medical device in a remote monitoring while reducing a risk for a patient involved with attending to the patient for activating a remote monitoring function within the implantable medical device.

At least this object is achieved by means of an implantable medical device comprising the features of claim 1.

Accordingly, the communication device, at the start of initial operation of the implantable medical device, is enabled to establish a communication with said remote monitoring system.

In one embodiment, the communication device is configured, for communicating with the remote monitoring system, to use a predefined communication protocol for transmitting information relating to, e.g., a measured physiological parameter to the remote monitoring system. The predefined communication protocol may, for example, be MICS (Medical Implant Communication Service), BLE (Bluetooth Low Energy), Zigbee, or a communication protocol of a band telemetry. The communication protocol may offer for a low power, low data rate, close proximity wireless data transmission.

In one embodiment, the implantable medical device is an implantable pulse generator (IPG) such as an implantable cardiac pacemaker, an implantable cardioverter-defibrillator (ICD), a cardiac resynchronization therapy device (CRT) like a cardiac resynchronization therapy pacemaker or a cardiac resynchronization therapy defibrillator, a neuro stimulator, an implantable loop recorder or an implantable insulin pump. The implantable medical device constitutes an active electronic implant which is configured to communicate, in an implanted state within a patient, with the remote monitoring system external to the patient, for example, using a short range communication technology.

Because the implantable medical device, from its initial start of operation, is enabled to establish a communication with a remote monitoring system, no particular activation of a communication function is required for including the implantable medical device into a remote monitoring. Rather, throughout its operative lifespan the implantable medical device is configured and enabled to establish a communication with a remote monitoring system, such that the implantable medical device may be included into a remote monitoring without modifying its programming configuration.

This allows to start a remote monitoring by simply delivering a remote monitoring system, such as a remote monitoring device, also denoted as a patient relay device, to the patient, upon which a communication with the implantable medical device is established automatically, without having to modify the implantable medical device. It hence is not required that the patient, for activating a remote monitoring function, visits a physician to accordingly program the implantable medical device. Rather, the implantable medical device from its start of operation is enabled to communicate with a remote monitoring system, such that the implantable medical device may be included in a remote monitoring at any time.

In one embodiment, the start of initial operation of the implantable medical device corresponds to an initial activation of the implantable medical device at or subsequent to implantation. That is, once the implantable medical device is activated following implantation into the patient, also the remote monitoring function is enabled, such that the implantable medical device is enabled to communicate with a remote monitoring system once the remote monitoring system is present.

If the implantable medical device is configured to remain operative within a patient in an implanted state over a time of operability, beneficially the communication device is enabled to establish a communication with a remote monitoring system over the entire time of operability, such that a remote monitoring system may be brought in operative communication connection with the implantable medical device at any time simply by delivering the remote monitoring system to the patient and bringing the remote monitoring system into a close proximity with the patient, upon which a communication in between the implantable medical device and the remote monitoring system is established automatically.

In one embodiment, the communication device is configured to transmit a transmit signal repeatedly according to a predefined first time scheme to establish a communication with a remote monitoring system. The transmit signal serves to trigger a communication with the remote monitoring system, wherein by means of the transmit signal, if received by a remote monitoring system, the communication is established and a data exchange in between the implantable medical device and the remote monitoring system becomes possible.

The implantable medical device may, for example, be configured to repeatedly transmit said transmit signal throughout its operation, wherein the communication device may be configured to await, subsequently to transmitting said transmit signal, a response signal from a remote monitoring system. If a response signal is received by the communication device, the implantable medical device is notified that a remote monitoring system in fact is present and enabled to communicate with the implantable medical device, upon which a communication in between the implantable medical device and the remote monitoring system for a data exchange may be established.

Because the implantable medical device transfers a transmit signal which may have the shape of a simple trigger command for triggering the remote monitoring system to respond, the repeated, continuous transmission of the transmit signal may take place at a low energy consumption, such that the search for the remote monitoring system by the implantable medical device does not substantially reduce the stored energy of the implantable medical device, in particular the energy stored within a battery of the implantable medical device. The operative lifespan of the implantable medical device is thus not substantially reduced due to enabling a communication with a remote monitoring system from the start of operation of the implantable medical device.

For example, in one embodiment, the operative lifespan of the implantable medical device is not reduced by more than 10%, preferably by more than 5%, even more preferably by more than 1% due to the continuous readiness of the implantable medical device to establish a communication with a remote monitoring system.

In one embodiment, the energy consumption of the implantable medical device for the search for a potentially present remote monitoring system may be less or equal 300 mWs per day, preferably less than or equal 100 mWs per day, even more preferably less than or equal 60 mWs per day, even more preferably 30 mWs per day, most preferably less than or equal 10 mWs per day.

In one embodiment, the predefined time scheme may be such that the communication device is configured to transmit said transmit signal at a predefined, regular time interval, for example, in a range between multiple hours and multiple days, for example, every 4 hours, 6 hours, 9 hours, 12 hours, once a day, every second day, every third day, every fourth day, every fifth day, every sixth day, once a week, once every two weeks and so on.

In contrast to a regular repetition interval, the predefined time scheme may be such that the transmit signal is transmitted by the communication device at a predefined pattern, for example, during predefined time ranges during a day or during a week. For example, the transmit signal may be transmitted by the communication device once or multiple times during the night, during the day, or for example, only during the weekend.

The repetition rate of the transmit signal determines how soon a connection in between the implantable medical device and a remote monitoring system, upon delivery to the patient, is established. The repetition rate, defined by the predefined time scheme, may be such that a communicative connection in between the implantable medical device and the remote monitoring system is established at the latest after one day upon activating the remote monitoring system in the presence of the implantable medical device, after three days, after one week, after two weeks, after three weeks, after four weeks, after one month, after two months or after more than two months.

In one embodiment, the transmit signal is configured to trigger the remote monitoring system to establish a communication connection to the implantable medical device. Upon receiving the transmit signal, the remote monitoring system hence initiates a procedure to establish communication with the implantable medical device, for example, for allocating a communication channel within a specified frequency band, for example, the MICS band in a range between 401 MHz to 406 MHz. Once the communication channel is established, the implantable medical device may communicate with the remote monitoring system, wherein the communication may be one directional from the implantable medical device to the remote monitoring system, for example, to transmit monitoring data, such as data relating to a status of the implantable medical device or a status of the patient. In another embodiment, the communication may be bi-directional in that the implantable medical device may communicate data towards the remote monitoring system, and in turn the remote monitoring system may transmit data towards the implantable medical device, for example, programming data or the like.

In one embodiment, the communication in between the implantable medical device and the remote monitoring system is established automatically once the remote monitoring system is brought into proximity of the implantable medical device and is activated in proximity to the implantable medical device. For activating the remote monitoring system, a device of the remote monitoring system, for example, a patient relay device, in one embodiment only needs to be plugged into a power connection, upon which the device is powered on and automatically establishes a communication with the implantable medical device.

In one embodiment, the implantable medical device is configured to initiate at least one communication function on the occasion of establishment of a communication connection with the remote monitoring system. Within the communication function, generally data may be transmitted from the implantable medical device to the remote monitoring system and/or from the remote monitoring system to the implantable medical device.

In one embodiment, within the communication function a data transmission may take place repeatedly, wherein the data transmission may take place according to a predefined, second time scheme, which for example, differs from the predefined first time scheme during the search for the remote monitoring system prior to establishing communication. In particular, once the implantable medical device has received a response from a remote monitoring system and hence is notified of the presence of the remote monitoring system, the implantable medical device may activate the communication function and may communicate with the remote monitoring system in a frequent manner according to the predefined second time scheme, for example, at regular second time intervals, which are substantially shorter than first time intervals used for transmitting transmit signals during the search phase for searching for a remote monitoring system.

The data communication herein may take place in transmission periods, wherein at the start of each transmission period a transmit signal may be sent by the implantable medical device, upon which the remote monitoring system responds with a response signal and establishes a communication connection, for example, by allocating a communication channel, such that a data transmission in between the implantable medical device and the remote monitoring system may take place.

Within the communication function, a repetition rate of data communication may, for example, lie in a range between 1 second and one day, for example, in between 1 minute and one hour. A data communication in between the implantable medical device and the remote monitoring system hence takes place, for example, once every few seconds, once every few minutes, or once every few hours.

Herein, for each data transmission in a transmission period the communication connection may be established anew, triggered by a transmit signal transmitted from the implantable medical device towards the remote monitoring system.

In one embodiment, the communication function is activated by the implantable medical device if and only if a specific activation criterion is fulfilled. The activation criterion may, for example, be that the last successful communication with the remote monitoring system may not be longer ago than one day, 2 days, 3 days, 4 days, 5 days, 6 days, one week, 2 weeks, 3 weeks, or one month.

An additional or alternative activation criterion may be that in a pre-defined previous time span a specified number of successful communication connections have been established in between the implantable medical device and the remote monitoring system, for example, within the last 2 days, the last 3 days, last 4 days, last 5 days, the last 6 days, last week, the last 2 weeks, the last 3 weeks, the last month, or the last 2 months. The predefined number of successful communication connections may lie in between 2 to 5 communication connections, preferably in between 2 to 10 communication connections, even more preferably in between 2 to 60 successful communication connections.

By means of the activation criterion it is ensured that not immediately upon a first connection to a remote monitoring system a specified communication function is enabled, but only if a stable, repeated communication in between the implantable medical device and the remote monitoring system is possible due to a continuous presence of the remote monitoring system in the vicinity of the implantable medical device.

In another aspect, a system comprises an implantable medical device of the type described above and a remote monitoring system for communicating with the implantable medical device. Whereas the implantable medical device may be activated to communicate with the remote monitoring system from its initial start of operation, in particular from the time of implanting the implantable medical device into a patient, the remote monitoring system may be delivered to the patient at a later point, wherein at the time of delivery and upon starting the operation of the remote monitoring system communication in between the remote monitoring system and the implantable medical device may be established automatically and without having to attend to configuring the implantable medical device or the remote monitoring system.

The remote monitoring system, in one embodiment, is configured to receive a transmit signal transmitted by the implantable medical device. Upon receiving the transmit signal, the remote monitoring system may initiate a channel allocation procedure in a specified frequency band for establishing a communication connection with the implantable medical device. Within the channel allocation procedure, the remote monitoring system may, for example, search and allocate for a communication channel in the respective frequency band, for example in the MICS band, wherein subsequently the allocated channel is used for data transmission in between the remote monitoring system and the implantable medical device.

Because the channel allocation takes place by the remote monitoring system, the implantable medical device only needs to send a trigger signal to the remote monitoring system, which requires limited energy, upon which the establishment of the communication connection substantially is carried out by the remote monitoring system. The implantable medical device hence does not need to search for a particular channel, but the communication initiation is substantially controlled by the remote monitoring system.

The system, in one embodiment, comprises an information system, also denoted as patient information system, which may be implemented by an external service center and may be in communication connection with the remote monitoring system, for example, via a public communication network, such as the Internet or a mobile communication network, such as a 2G, 3G, 4G, or 5G communication network. The information system may serve to process data received from the remote monitoring system and to make the data available for example to healthcare personnel, for example, by providing access to the data via a web interface or the like.

In yet another aspect, a method for operating an implantable medical device comprises: providing said implantable medical device, the implantable medical device including a functional device for carrying out a therapeutic or diagnostic function, and a communication device for communicating with a remote monitoring system; wherein the step of providing said implantable medical device includes that the communication device, at a start of initial operation of the implantable medical device, is enabled to establish a communication with said remote monitoring system.

The advantages and advantageous embodiments described above for the implantable medical device equally apply also to the method, such that it shall be referred to the above in this respect.

Because the implantable medical device from its start of initial operation is enabled to communicate with a remote monitoring system, a remote monitoring may be initiated at any time simply by bringing the remote monitoring system into operative proximity with the implantable medical device, upon which the communication in between the implantable medical device and the remote monitoring system is established automatically. This allows for including an implantable medical device into a remote monitoring simply by delivering a remote monitoring system, such as a patient relay device, to the patient, without having to attend to perform any programming action on the implantable medical device prior to initiating the remote monitoring.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The idea(s) behind the present invention shall subsequently be explained in more detail by referring to the embodiments shown in the figures. Herein.

DETAILED DESCRIPTION

Figure 1:
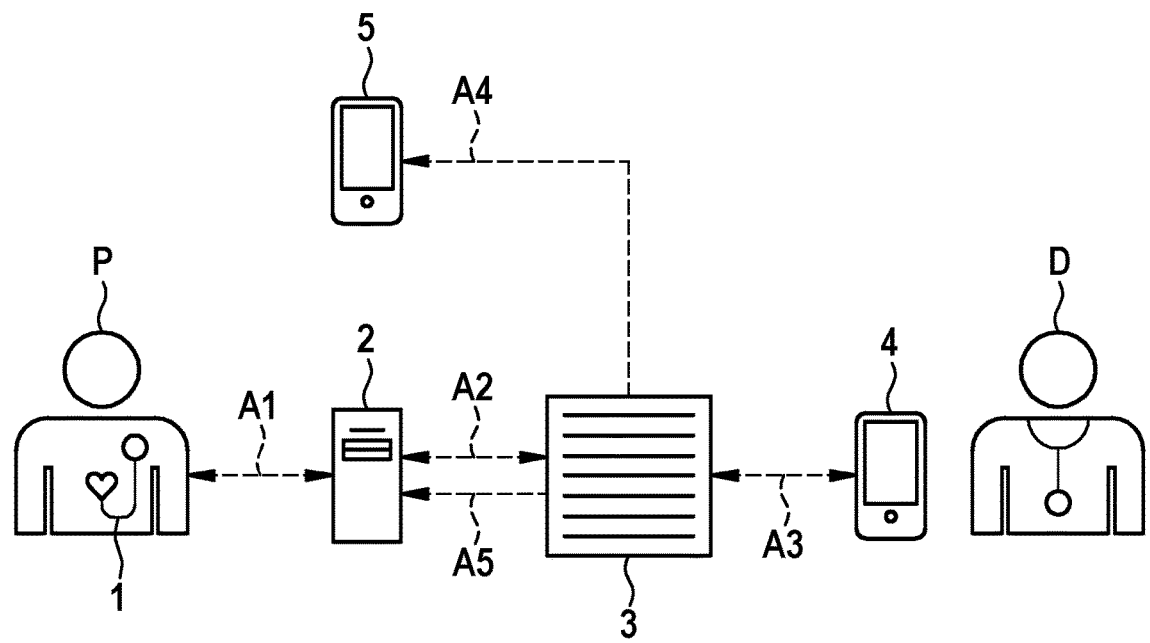
FIG. 1 shows a schematic view of a system for a remote (home) monitoring of a patient carrying an implantable medical device.

FIG. 1 shows a schematic illustration of a system for a remote (home) monitoring of a patient P carrying an implantable medical device 1.

The system comprises an implantable medical device 1 implanted in a patient P, the implantable medical device 1, for example, being a cardiac stimulation devices such as a pacemaker device or a defibrillator device, for example, an implantable pulse generator (IPG) such as an implantable cardiac pacemaker, an implantable cardioverter-defibrillator (ICD), a cardiac resynchronization therapy device (CRT) such as a cardiac resynchronization therapy pacemaker or a cardiac resynchronization therapy defibrillator, a neuro stimulator, an insulin pump or an implantable loop recorder or any other implantable active electronic device for performing a therapeutic or diagnostic function within a patient P.

The implantable medical device 1 constitutes an active electronic implant which is configured and enabled to communicate, in an implanted state within a patient P, with a remote monitoring system 2 external to the patient P. The remote monitoring system 2 may comprise one or multiple portable devices, also denoted as patient relay devices having the shape of mobile communication-enabled devices, which are placed in the home of the patient P and serve to communicate with the implantable medical device 1 to exchange information with the implantable medical device 1 using a communication path A1, for example, according to a communication technology using the MICS protocol, the BLE protocol or the Zigbee protocol.

The remote monitoring system 2 is, in one embodiment, in communication connection with an information system 3 by means of a communication path A2, the communication path A2 being established, for example, via a public communication network such as the Internet or a telecommunications network, for example, a mobile communication network such as a 2G, 3G, 4G or 5G telecommunications network. The remote monitoring system 2 generally functions as a relay to transmit information from the implantable medical device 1 to the information system 3, or from the information system 3 to the implantable medical device 1.

The information system 3 may be configured to process data received from the implantable medical device 1 via the remote monitoring system 2. Processed data may be provided to an access device 4 of healthcare personnel, for example a physician D, via a communication path A3, for example, by means of a web interface to which the access device 4 may connect for accessing the data on the information system 3. In addition, the information system 3 may provide messages, such as alert messages, to a specified communication terminal 5 belonging, for example, to the patient P or a person familiar with the patient P via a data communication path A4, and to the remote monitoring system 2 via a communication path A5.

The implantable medical device 1 generally is configured to perform a function in a patient over a prolonged period of time, such as a measurement function or a cardiac or neuronal stimulation function. For example, the medical device 1 shall remain functional within in a patient for multiple years and in this course shall record and communicate measurement data to the remote monitoring system 2, so that the measurement data may be used to diagnose or monitor the condition of the patient.

Figure 2:
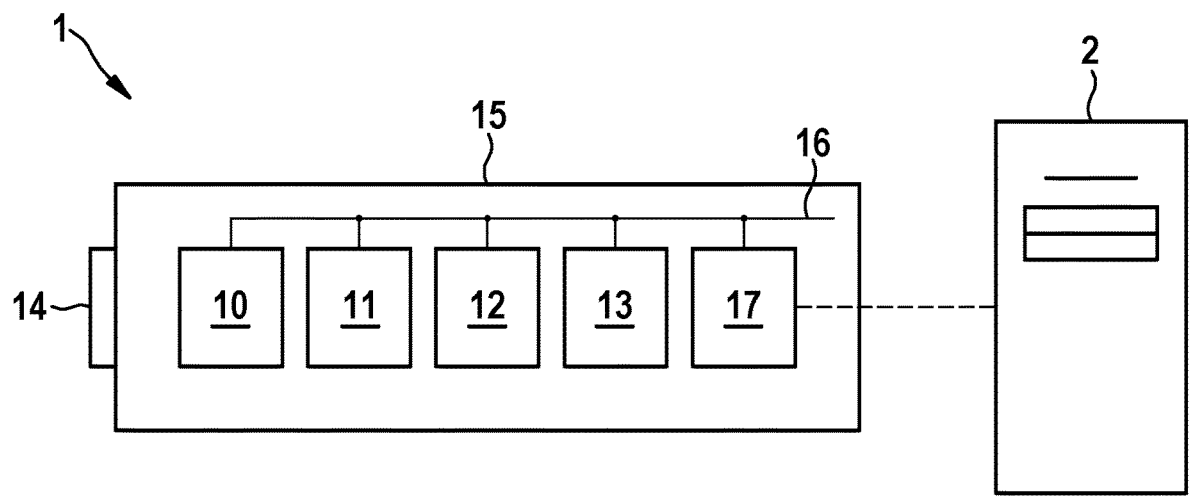
FIG. 2 shows a schematic view of an implantable medical device.

Such an implantable medical device 1 generally is small in size. As schematically shown in FIG. 2, the medical device 1, for example, comprises a housing 15 encompassing an electronic functional device 10 which is formed, for example, by a processor and serves to perform a predetermined function, for example, a measuring function or a therapy function. The medical device 1 in addition comprises a memory 11, e.g., in the form of a RAM (Random Access Memory), (optionally) a wake-up device 12, an energy storage 13, for example in the form of a battery, and a communication device 17 for communicating with remote monitoring system 2. The different functional units are encapsulated in the housing 15 in a fluid-tight manner and are interconnected, for example, by a bus system 16 for a data exchange in between the different devices.

The medical device 1 in addition, in the shown embodiment, comprises a measurement sensor 14, which is used together with the functional device 10 to perform a measurement in order to record one or multiple physiological parameters, for example, to measure the patient's body temperature, the heart rate, the heart rate at rest, respiration parameters, an activity parameter or other parameters within the patient P. Measurements may be repeatedly performed in predetermined measurement periods, with measurement data being stored, e.g., temporarily in the memory 11 during a measurement and communicated to the remote monitoring system 2 via the communication device 17.

The measurement sensor 14 may, for example, be an electrode which is in contact with tissue in the vicinity of the implanted medical device 1, or which is placed on a lead extending from the medical device 1 towards a location of interest. By means of the measurement sensor 14, for example, an electrocardiogram signal may be recorded, the electrocardiogram signal allowing for a sensing of the heart rate and the heart rate at rest.

In order to reduce the energy consumption of the medical device 1, in one embodiment the functional device 10 or certain functions of the functional device 10 possibly do not operate continuously and at all times, but may be switched from a switched-off state to an operational state when required in order to carry out a function in the operational state. In the switched-off state the functional device 10 or certain functions may be switched off. In order to transfer the functional device 10 or certain functions of the functional device 10 from the switched-off state to the operational state, the wake-up device 12 is provided, which serves to switch on the functional device 10 or certain functions of the functional device 10 based on a signal provided, e.g., from an external activator device, such as the remote monitoring system 2.

Generally, when an implantable medical device 1 shall be included in a remote monitoring using a remote monitoring system 2, a patient P carrying an implantable medical device 1 needs to visit a physician, which generally has to access the implantable medical device 1 by means of a programming device in order to activate a communication function, thus enabling the implantable medical device to communicate with a remote monitoring system 2. After activation, a communication in between the implantable medical device 1 and the remote monitoring system 2 may be established, such that data may be exchanged in between the implantable medical device 1 and the remote monitoring system 2.

E.g., in a situation of a general pandemic, such as the COVID-19 pandemic, there is a general desire to keep the risk for a patient P as low as possible, in particular avoiding any unnecessary, potentially risky contacts for the patient P. Hence, there is a desire to avoid a necessity for the patient P to visit a physician in order to activate a remote monitoring function of the implantable medical device 1.

For this it is proposed that the communication device 17 of the implantable medical device 1, from the initial start of operation of the implantable medical device 1, is enabled to establish a communication with a remote monitoring system 2. Hence, from its start of operation the implantable medical device 1 is enabled to communicate with a remote monitoring system 2, such that no particular activation is required if the implantable medical device shall, at any time, be included in a remote (home) monitoring.

The implantable medical device 1 hence, over its entire life span, is enabled to detect the presence of a remote monitoring system 2, and if a remote monitoring system 2 is present, the implantable medical device 1 may initiate a communication in between the remote monitoring system 2 and the implantable medical device 1. Accordingly, if a remote monitoring shall be started, it only is required to deliver the remote monitoring system 2, for example, a remote monitoring device in the shape of a so-called patient relay device, to the patient P, upon which the patient P starts operation of the remote monitoring system 2 by plugging the remote monitoring system 2 into a power connection and switching on the remote monitoring system 2. Once the implantable medical device 1 detects the presence of the remote monitoring system 2, communication may be started, and data may be exchanged in a one-directional or bi-directional fashion in between the implantable medical device 1 and the remote monitoring system 2.

Figure 3:
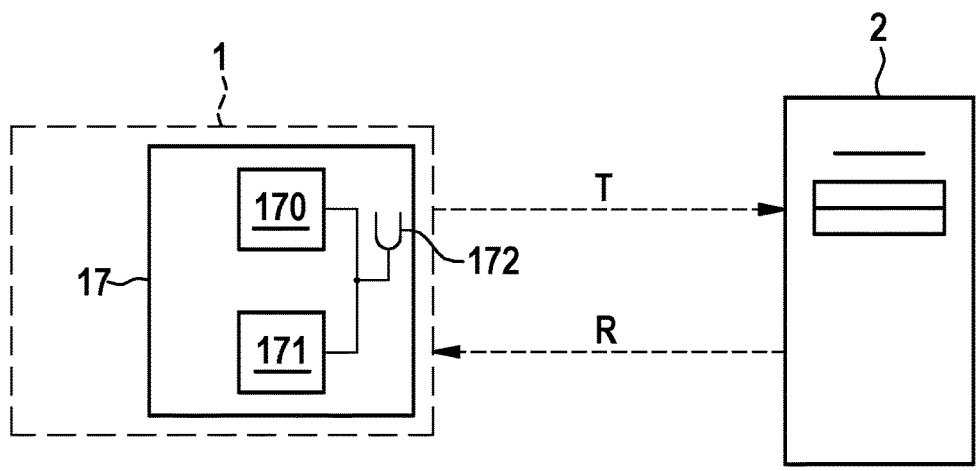
FIG. 3 shows a schematic drawing of a communication device of an implantable medical device in communication with a remote monitoring system.

Referring now to FIG. 3, in one embodiment a communication in between the implantable medical device 1 and the remote monitoring system 2 may be established in that the implantable medical device 1 triggers the remote monitoring system 2 to establish the communication. For example, the communication device 17 of the implantable medical device 1 may comprise a transmitter 170 for transmitting a transmit signal T towards the remote monitoring system 2, and a receiver 171 for receiving a response signal R from the remote monitoring system 2. The transmitter 170 and the receiver 171 may use a common antenna 172 for transmitting respectively receiving signals, wherein the communication device 17 may use a specified frequency band, for example, the MICS band in between 401 MHz and 406 MHz, to communicate with the remote monitoring system 2 according to the MICS protocol.

Figure 4:
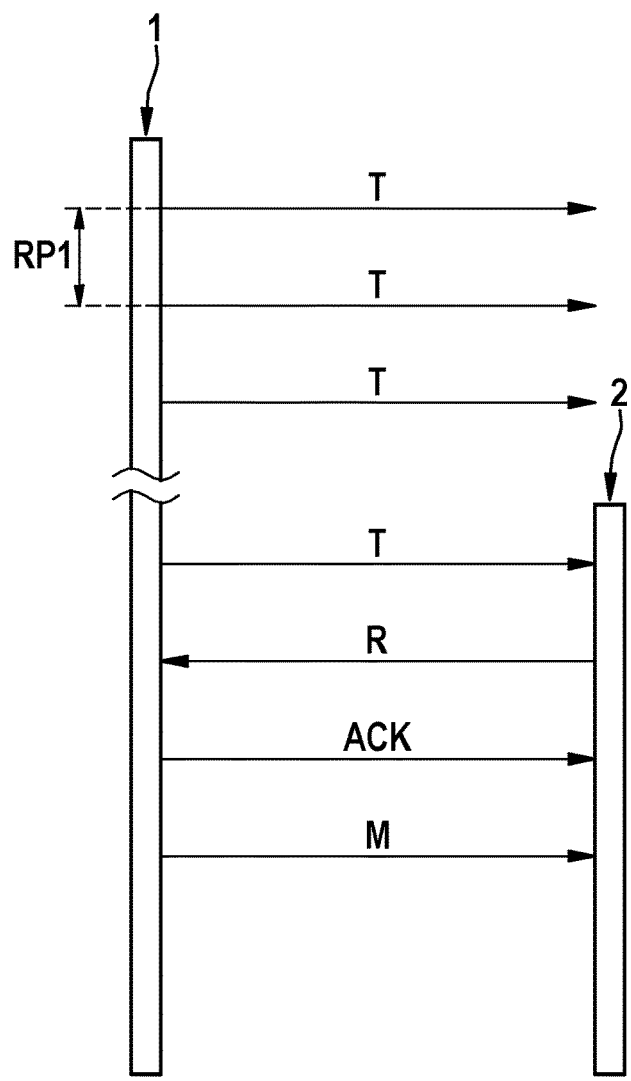
FIG. 4 shows a schematic flow diagram of establishing a communication between an implantable medical device and a remote monitoring system.

Referring now to FIG. 4, in one embodiment the implantable medical device 1 is configured to repeatedly send out transmit signals T according to a predefined time scheme, for example, at a fixed repetition rate RP1, for example, once every few hours, once a day or once a week. The transmit signal T in each case may have the shape of a simple triggering command, the transmit signal T causing the remote monitoring system 2, upon reception, to initiate a channel allocation procedure for establishing a communication channel for communicating with the implantable medical device 1.

In one embodiment, the implantable medical device 1 repeatedly transmits the transmit signal T and awaits a response signal R from a remote monitoring system 2. If no response signal R is received, no further action is taken at the implantable medical device 1 for establishing a communication, until another transmit signal T is transmitted according to the predefined time scheme.

As the transmit signal T may have a simple shape, and as a reception window, during which the receiver 171 is active, for receiving a response signal R following the transmission of a transmit signal T may be short, the repeated transmission of the transmit signal T to trigger a communication with a remote monitoring system 2 may take place energy efficiently, requiring, for example, in one embodiment, a current consumption of less than 20 mAs per day, beneficially less than 10 mAs per day.

If the overall energy capacity of the energy storage 13 is, for example, 800 mAs and the estimated overall life span of the implantable medical device 1 without the search function for establishing a communication with a remote monitoring system 2 is 12 years, a current consumption of, for example, 5.6 mAs per day for the search for a remote monitoring system 2 represents a reduction of the operative lifespan of the implantable medical device 1 by less than 1% (37 days). The search function for triggering a communication with a remote monitoring system 2 hence does not substantially reduce the lifespan of the implantable medical device 1.

If, at a certain time, a remote monitoring system 2 is present, as shown in FIG. 4, the remote monitoring system 2 receives the transmit signal T, upon which the remote monitoring system 2 initiates a channel allocation procedure and establishes a communication channel, for example, a channel or a combination of channels within the MICS band. In the course of the channel allocation, the remote monitoring system 2 sends a response signal R to the implantable medical device 1 for agreeing on the communication channel (in a hand-shake type fashion), upon which the implantable medical device 1 may reply with an acknowledgment signal ACK, hence concluding the channel allocation. Once the communication channel is established, data messages M may be exchanged, for example, one-directionally from the remote implantable medical device 1 to the remote monitoring system 2, or bi-directionally in between the implantable medical device 1 and the remote monitoring system 2.

Figure 5:
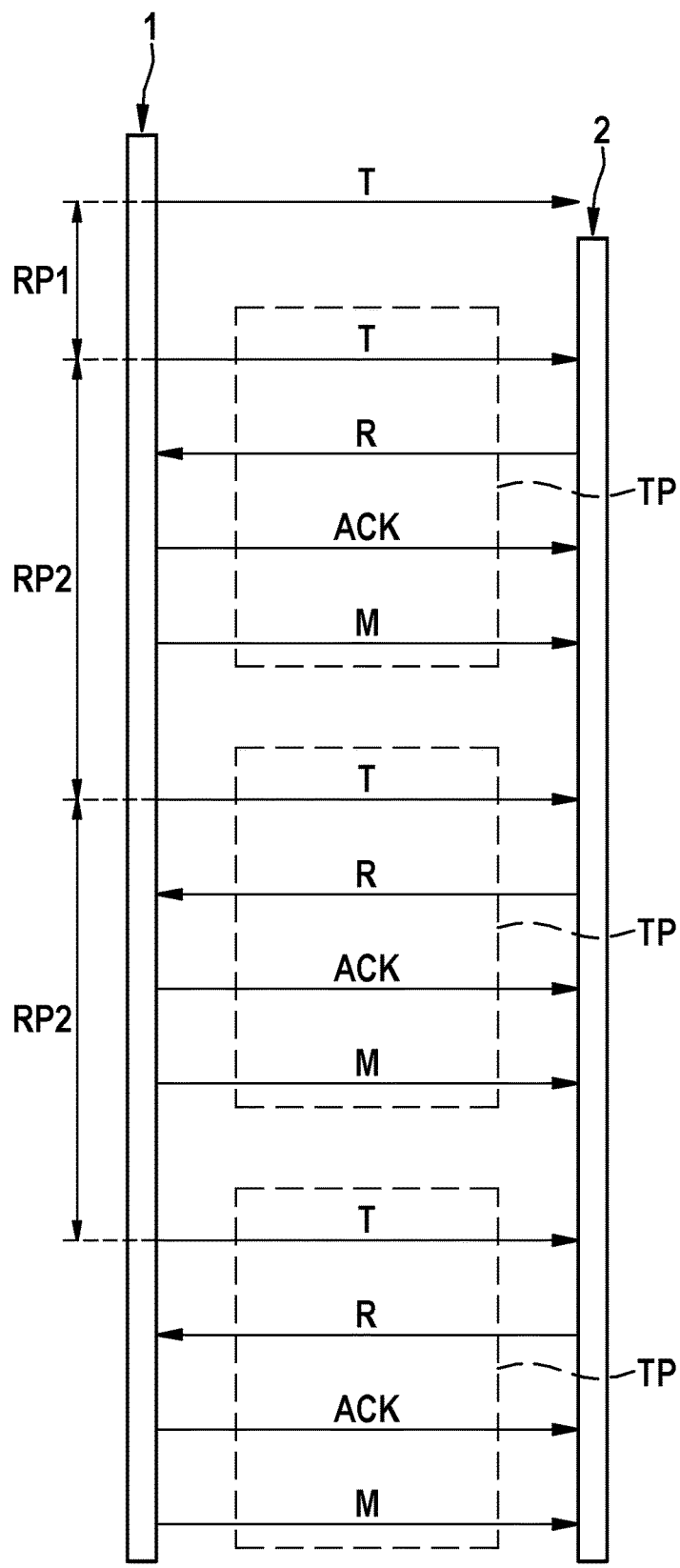
FIG. 5 shows a schematic flow diagram of a communication function for communicating between an implantable medical device and a remote monitoring system.

Referring now to FIG. 5, in case a communication in between the implantable medical device 1 and a remote monitoring system 2 is established and hence the implantable medical device 1 knows about the presence of a remote monitoring system 2, the implantable medical device 1 may switch on a communication function in order to exchange data with the remote monitoring system 2. The activation of the communication function herein may take place immediately at the first time that a remote monitoring system 2 is detected to be present, or may take place according to one or multiple defined activation criteria, requiring, for example, that in a predefined previous time span a specified number of successful communication connections have been established in between the implantable medical device 1 and the remote monitoring system 2, for example, ten communication connections in the last week or so.

Within the communication function, a data transmission one-directionally from the implantable medical device 1 to the remote monitoring system 2 or bi-directionally in between the implantable medical device 1 and the remote monitoring system 2 may take place according to a second time scheme different than the time scheme according to which the transmit signals T have been sent in the search phase by the implantable medical device 1 when searching for the presence of a remote monitoring system 2.

As illustrated in FIG. 5, once the communication function is activated by the implantable medical device 1, a data transmission may take place in transmission periods TP, for example, at a repetition rate RP2 which is smaller than the repetition rate RP1 at which the transmit signals T have been sent during the search phase when searching for the remote monitoring system 2. Within each transmission period TP, herein, a data transmission is initiated by a transmit signal T sent by the implantable medical device 1, upon which the remote monitoring system 2 responds with a response signal R and awaits an acknowledgment signal ACK from the implantable medical device 1 to allocate a communication channel for communicating with the implantable medical device 1. Each transmission period TP hence is triggered by the implantable medical device 1, upon which a channel allocation procedure is performed by the remote monitoring system 2.

The idea(s) underlying the present invention is not limited to the embodiments described above, but may be implemented in an entirely different fashion.

Because an implantable medical device over its entire lifespan is enabled to communicate with a remote monitoring system, the implantable medical device may be included in a remote monitoring at any time, requiring simply a delivery of the remote monitoring system towards the patient, upon which a communication with the implantable medical device is established automatically. A patient hence does not have to attend to a physician in order to activate a remote monitoring function of the implantable medical device, hence reducing a logistical burden and a health risk for the patient.

As the search function of the implantable medical device for searching for a remote monitoring system may be implemented in an energy efficient way, the continuous enablement of the implantable medical device to be included in a remote monitoring does not significantly shorten the lifespan of the implantable medical device.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Implantable medical device
10 Functional device
11 Memory device
12 Wake-up device
13 Energy storage
14 Sensor device
15 Housing
16 Bus system
17 Communication device
170 Transmitter 171 Receiver
172 Antenna
2 Patient monitoring device
3 Monitoring service center
4 Access device
5 Communication terminal
A1-A5 Communication path
ACK Acknowledgement message
D Physician
M Data message
P Patient
R Response signal
RP1, RP2 Repetition interval
T Transmit signal
TP Transmission period

The invention claimed is:

1. An implantable medical device, comprising: a functional device for carrying out a therapeutic or diagnostic function, and a communication device for communicating with a remote monitoring system, wherein the communication device, at a start of initial operation of the implantable medical device, is enabled to establish a communication with said remote monitoring system,
   wherein the communication device is configured to transmit a transmit signal repeatedly according to a pre-defined first time scheme to establish a communication with said remote monitoring system,
   wherein the communication device is configured to transmit said transmit signal repeatedly at a regular first time interval to establish a communication with said remote monitoring system,
   wherein said transmit signal is configured to trigger said remote monitoring system to establish a communication connection to the implantable medical device,
   wherein the repeated transmission of the transmit signal requires a current consumption of less than 20 mAs per day,
   wherein the implantable medical device is configured to:
      initiate at least one communication function on the occasion of establishment of a communication connection with the remote monitoring system, and
   activate the at least one communication function only if a specific activation criterion is fulfilled, the activation criterion is that in a pre-defined previous time span a specified number of successful communication connections have been established in between the implantable medical device and the remote monitoring system.

2. The implantable medical device of claim 1, wherein the communication device is configured to communicate with the remote monitoring system using a pre-defined communication protocol.

3. The implantable medical device of claim 2, wherein the communication protocol is MICS, BLE or Zigbee.

4. The implantable medical device of claim 1, wherein the start of initial operation corresponds to an initial activation of the implantable medical device at or subsequent to implantation.

5. The implantable medical device of claim 1, wherein the implantable medical device is configured to remain operative within a patient over a time of operability, wherein the communication device is enabled to establish said communication with said remote monitoring system over the entire time of operability.

6. The implantable medical device of claim 1, wherein the implantable medical device is configured, within the at least one communication function, to transmit monitoring data to the remote monitoring system.

7. The implantable medical device of claim 1, wherein the implantable medical device is configured, within the at least one communication function, to transmit monitoring data to the remote monitoring system repeatedly according to a predefined, second time scheme.

8. The implantable medical device of claim 1, wherein the implantable medical device is configured, within the at least one communication function, to repeatedly transmit monitoring data to the remote monitoring system at a regular, second time interval.

9. The implantable medical device of claim 1, wherein the activation criterion is that the last successful communication with the remote monitoring system may not be longer ago than one month.

10. A system comprising an implantable medical device of claim 1 and a remote monitoring system for communicating with the implantable medical device.

11. The system of claim 10, wherein the remote monitoring system is configured to receive a transmit signal from the implantable medical device and to initiate a channel allocation procedure in a specified frequency band for establishing a communication connection with the implantable medical device.

12. A method for operating an implantable medical device, comprising: providing said implantable medical device, the implantable medical device including a functional device for carrying out a therapeutic or diagnostic function, and a communication device for communicating with a remote monitoring system; wherein said step of providing said implantable medical device includes that the communication device, at a start of initial operation of the implantable medical device, is enabled to establish a communication with said remote monitoring system,
   wherein the communication device is configured to transmit a transmit signal repeatedly according to a pre-defined first time scheme to establish a communication with said remote monitoring system,
   wherein the communication device is configured to transmit said transmit signal repeatedly at a regular first time interval to establish a communication with said remote monitoring system,
   wherein said transmit signal is configured to trigger said remote monitoring system to establish a communication connection to the implantable medical device,
   wherein the repeated transmission of the transmit signal requires a current consumption of less than 20 mAs per day,
   wherein the implantable medical device is configured to:
      initiate at least one communication function on the occasion of establishment of a communication connection with the remote monitoring system, and
   activate the at least one communication function only if a specific activation criterion is fulfilled, the activation criterion is that in a pre-defined previous time span a specified number of successful communication connections have been established in between the implantable medical device and the remote monitoring system.

* * * * *